US009803262B2

(12) United States Patent
Goto et al.

(10) Patent No.: US 9,803,262 B2
(45) Date of Patent: *Oct. 31, 2017

(54) GALLIUM EXTRACTION AGENT AND GALLIUM EXTRACTION METHOD

(71) Applicants: Kyushu University, National University Corporation, Fukuoka-shi, Fukuoka (JP); SUMITOMO METAL MINING CO., LTD., Tokyo (JP)

(72) Inventors: Masahiro Goto, Fukuoka (JP); Fukiko Kubota, Fukuoka (JP); Yuzo Baba, Fukuoka (JP)

(73) Assignees: Kyushu University, National University Corporation, Fukuoka-shi (JP); SUMITOMO METAL MINING CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/423,061

(22) PCT Filed: Apr. 26, 2013

(86) PCT No.: PCT/JP2013/062481
§ 371 (c)(1),
(2) Date: Feb. 20, 2015

(87) PCT Pub. No.: WO2014/030395
PCT Pub. Date: Feb. 27, 2014

(65) Prior Publication Data
US 2015/0211093 A1    Jul. 30, 2015

(30) Foreign Application Priority Data
Aug. 20, 2012 (JP) ................ 2012-181885

(51) Int. Cl.
| | | |
|---|---|---|
| C22B 58/00 | (2006.01) | |
| C22B 3/26 | (2006.01) | |
| B01D 11/04 | (2006.01) | |
| C07C 237/06 | (2006.01) | |
| C07D 233/64 | (2006.01) | |
| C22B 3/08 | (2006.01) | |
| C22B 3/44 | (2006.01) | |

(52) U.S. Cl.
CPC .......... *C22B 58/00* (2013.01); *B01D 11/0492* (2013.01); *C07C 237/06* (2013.01); *C07D 233/64* (2013.01); *C22B 3/0005* (2013.01); *C22B 3/0032* (2013.01); *C22B 3/08* (2013.01); *C22B 3/44* (2013.01); *Y02P 10/234* (2015.11); *Y02P 20/582* (2015.11)

(58) Field of Classification Search
CPC ....... C22B 58/00; C22B 19/26; C07C 237/06; B01D 11/0492; C07D 233/64
USPC ......... 423/112; 252/184; 548/341.5; 562/565
See application file for complete search history.

(56) References Cited

U.S. PATENT DOCUMENTS

| | | | |
|---|---|---|---|
| 5,250,517 A * | 10/1993 | Branca | ................ C07D 233/64 530/330 |
| 6,267,936 B1 | 7/2001 | Delmas et al. | |
| 6,709,641 B1 | 3/2004 | Gutknecht et al. | |
| 8,951,486 B2 * | 2/2015 | Goto et al. | ................ 423/21.5 |
| 9,011,804 B2 * | 4/2015 | Goto et al. | ................ 423/150.1 |
| 9,458,526 B2 | 10/2016 | Goto et al. | |
| 2005/0124765 A1 | 6/2005 | Seko et al. | |
| 2007/0248514 A1 | 10/2007 | Cheng et al. | |
| 2013/0102806 A1 | 4/2013 | Sakaki et al. | |
| 2014/0234187 A1 | 8/2014 | Goto et al. | |
| 2014/0328737 A1 | 11/2014 | Goto et al. | |
| 2015/0315674 A1 | 11/2015 | Goto et al. | |

FOREIGN PATENT DOCUMENTS

| | | |
|---|---|---|
| AU | 725800 B2 | 8/2000 |
| CN | 101519427 A | 9/2009 |
| CN | 103582711 A | 2/2014 |
| CN | 104822851 A | 8/2015 |
| EP | 0834581 A1 | 4/1998 |
| EP | 2679693 A1 | 1/2014 |
| EP | 2682486 A1 | 1/2014 |
| EP | 2712940 A1 | 4/2014 |

(Continued)

OTHER PUBLICATIONS

Pajewski, et al., "The effect of midpolar regime . . . heptapeptides" New Journal of Chemistry, 2007, 31, pp. 1960-1972.*
Kunitake, et al., "Regulation of catalytic . . . membranes" Studies in Organic Chemistry, 1983, 13 (Biomimetic Chem.), pp. 147-162.*
International Search Report of PCT/JP2013/062481 dated Jul. 9, 2013.
Morizono, Hirofumi et al.; "Liquid-liquid extraction of transition metal ions with an alkylhistidine Extractant"; Separation and Purification Technology, Jul. 29, 2011, vol. 80, No. 2, pp. 390-395.
Robert Pajewski et al., "The effect of midpolar regime mimics on anion transport mediated by amphiphilic heptapeptides," New Journal of Chemistry, 2007, 1960-1972.
Office Action dated Nov. 23, 2015, issued for China Patent Application No. 201380042793.7.
K. Shimojo et al., "Extraction behavior and separation of lanthanides with a diglycol amic acid derivative and a nitrogen-donor ligand," Anal. Sci., vol. 23, Dec. 2007, pp. 1427-1430.
Office Action for JP Application No. 2013-084951 dated Jan. 14, 2014.
CAS Registration No. 1156229-80-9.

(Continued)

*Primary Examiner* — Steven Bos
(74) *Attorney, Agent, or Firm* — Locke Lord LLP (57) ABSTRACT

Provided are an extraction agent and extraction method that selectively extract and, at a low cost, recover gallium from an acidic solution containing gallium and zinc. The gallium extraction agent comprises an amide derivative represented by general formula (I). In the formula, $R^1$ and $R^2$ each indicate the same or different alkyl group, $R^3$ indicates a hydrogen atom or an alkyl group, and $R^4$ indicates a hydrogen atom or any given group, other than an amino group, bonded to the α-carbon as an amino acid. The general formula preferably has a glycine unit, a histidine unit, a lysine unit, an aspartic acid unit, or an N-methylglycine unit. By extracting gallium from an acidic solution containing gallium and zinc by means of solvent extraction using the extraction agent, it is possible to selectively extract gallium.

19 Claims, 6 Drawing Sheets

(56) References Cited

FOREIGN PATENT DOCUMENTS

| | | |
|---|---|---|
| JP | 04-074711 A | 3/1992 |
| JP | 06-200336 A | 7/1994 |
| JP | 09-143589 A | 6/1997 |
| JP | H-09-291320 A | 11/1997 |
| JP | 2000-212658 A | 8/2000 |
| JP | 2000-234130 A | 8/2000 |
| JP | 2000-313928 A | 11/2000 |
| JP | 2002-539324 A | 11/2002 |
| JP | 2007327085 A | 12/2007 |
| JP | 2009256291 A | 11/2009 |
| JP | 2010-174366 A | 8/2010 |
| JP | 2012-102062 A | 5/2012 |
| JP | 2013-216656 A | 10/2013 |
| WO | 2005/073415 A1 | 8/2005 |
| WO | WO-2012/005183 A1 | 1/2012 |
| WO | WO-2013/069562 A1 | 5/2013 |
| WO | WO-2013/069563 A1 | 5/2013 |
| WO | WO-2013/136941 A1 | 9/2013 |
| WO | WO-2014/148431 A1 | 9/2014 |

OTHER PUBLICATIONS

EESR for EP Application No. 12848105.8 dated Jan. 22, 2014.
Naganawa H, et al: "A New "Green" Extractant of the Diglycol Amic Acid Type for Lanthanides", Solvent Extraction Research and Development, Japan, Japanese Association of Solvent Extraction, Saga, JP, vol. 14, Jan. 1, 2007, pp. 151-159.
Singh D K et al: "Extraction of rare earths and yttrium with high molecular weight carboxylic acids", Hydrometallurgy, Elsevier Scientific Publishing CY. Amsterdam, NL, vol. 81, No. 3-4, Mar. 1, 2006, pp. 174-181.
EESR for EP Application No. 12847107.5 dated Feb. 6, 2014.
Holger Stephan et al: "Liquid-Liquid Extraction of Metal Ions with Amido Podands", Solvent Extraction and Ion Exchange, Taylor & Francis Group LLC, US, vol. 9, No. 3, Jan. 1, 1991, pp. 459-469.
Office Action for JP Application No. 2014-022868 dated Apr. 8, 2014.
CAS Registration No. 1153237-54-7.
CAS Registration No. 1153399-39-3.
CAS Registration No. 1178468-85-3.
CAS Registration No. 1179174-30-1.
CAS Registration No. 1182789-10-1.
CAS Registration No. 1183588-00-2.
CAS Registration No. 1291231-35-0.
EESR for EP Application No. 13761717.1 dated Oct. 14, 2014.
Yuzo Baba et al., "Development of Novel Extractants with Amino Acid Structure for Efficient Separation of Nickel and Cobalt from Manganese Ions", Industrial & Engineering Chemistry Research, vol. 53, No. 2, Dec. 25, 2013, pp. 812-818.
Smith B F et al., "Amides as phase modifiers for N,N'—tetraalkylmalonamide extraction of actinides and lanthanides from nitric acid solutions", Separation Science and Technology, Dekker, New York, NY, US, vol. 32, Jan. 1, 1997, pp. 149-173.
Office Action for U.S. Appl. No. 14/130,283 dated Feb. 26, 2015.
Office Action for CN Application No. 201380002904.1 dated Jun. 26, 2015.
Office Action for CN Application No. 201480008628.4 dated Mar. 10, 2016.
EESR for EP Application No. 14770382.1 dated Feb. 16, 2016.
Office Action for U.S. Appl. No. 14/765,307 dated Apr. 6, 2016.
Office Action dated Feb. 17, 2017, issued for U.S. Appl. No. 14/650,364.
Bourget C et al., "Cyanex® 301 binary extractant systems in cobalt/nickel recovery from acidic sulphate solutions", Hydrometallurgy, Elsevier Scientific Publishing CY. Amsterdam, NL, vol. 77, No. 3-4, 1 Jun. 1, 2005, pp. 203-218, XP027652523.
J.M. Zhao et al., "Synergistic extraction and separation of valuable metals from waste cathodic material of lithium ion batteries using Cyanex272 and PC-88A", Separation and Purification Technology, vol. 78, No. 3, 1 Apr. 1, 2011, pp. 345-351, XP055013869.
Extended European Search Report dated Nov. 20, 2015, issued for European Patent Application No. 13862883.9.
International Search Report dated Nov. 26, 2013, issued for International Application No. PCT/JP2013/074158.

* cited by examiner

GALLIUM EXTRACTION AGENT AND GALLIUM EXTRACTION METHOD

TECHNICAL FIELD

The present invention relates to a gallium extraction agent and a gallium extraction method, more particularly, an extraction agent and an extraction method, which efficiently isolate and extract gallium from an acidic solution containing gallium and zinc.

BACKGROUND ART

Gallium is supplied in the form of alloy targets with zinc and tin and paste as a material for transparent conductive films such as a semiconductor device and a touch panel and is widely used.

Ores incidentally contain gallium in a very slight amount and also gallium is unevenly distributed. So it is not easy to ensure a stable supply of gallium. In addition, ores containing gallium contain lead and zinc in a grossly excessive amount as compared to the amount of gallium in many cases. Thus, when recovering gallium there is a great problem with efficiently separating gallium from lead and zinc.

Therefore, gallium is obtained from ores, and furthermore gallium is also obtained by recovering electronic circuit boards discarded in the city, defective items produced in production processes and other target materials which have been effectively finished and the like and recycling these. When the discarded electronic circuit boards and the like are recycled to obtain gallium, however, there is still a problem with efficiently separating gallium from lead and zinc.

As a method for separating gallium from lead and zinc, a solution obtained by a two-stage neutralization treatment during the zinc leaching residue treatment step of zinc smelting is used as a solution to be extracted containing gallium and indium, and this solution to be extracted is adjusted to pH 2.4 to 3.6. Separately, a chelating agent is added to an organic solvent, and an extraction organic solvent having an organic phase in which a part of the protons in this chelating agent is substituted by an alkaline earth metal is also prepared. It is proposed that both these solutions be mixed to extract and isolate gallium and gallium in the above solution to be extracted (see Patent Document 1). The method described in Patent Document 1, however, cannot be directly applied to a solution leached using an acid, for example, a low pH solution with a pH less than 2, and costs for a neutralizer to adjust pH, neutralization equipment, and much time for treatment are required.

It is also suggested that indium, gallium and zinc are each isolated using a chelating extraction agent having phosphinic acid as a ligand (see Patent Document 2). The invention described in Patent Document 2, however, has high selectivity to zinc in coexistence with cadmium. Accordingly, when it is required to separate gallium from zinc out of members not using cadmium like modern electronic members, it cannot be said that gallium is efficiently obtained.

Patent Document 1: Japanese Unexamined Patent Application, Publication No. 2000-212658
Patent Document 2: Japanese Unexamined Patent Application, Publication No. 2009-256291

DISCLOSURE OF THE INVENTION

Problems to be Solved by the Invention

An object of the present invention is to provide an extraction agent and an extraction method which selectively extract and, at a low cost, recover gallium from an acidic solution containing gallium and zinc.

As a result of repeated intensive research to solve the above problems, the present inventors found that the above object could be achieved by providing an gallium extraction agent comprising an amide derivative represented by the following general formula (I), thereby completing the present invention.

Means for Solving the Problems

Specifically, the following are provided in the present invention.

(1) The present invention is a gallium extraction agent comprising an amide derivative represented by the following general formula (I):

(wherein $R^1$ and $R^2$ each represents the same or different alkyl group, the alkyl group may be a straight chain or a branched chain, $R^3$ represents a hydrogen atom or an alkyl group, and $R^4$ represents a hydrogen atom or any group other than an amino group which is bound to the α carbon as an amino acid).

(2) In addition, the present invention is the gallium extraction agent according to (1), wherein the amide derivative is any one or more of a glycine amide derivative, a histidine amide derivative, a lysine amide derivative, an aspartic acid amide derivative and a N-methylglycine derivative.

(3) In addition, the present invention is a gallium extraction method, wherein gallium is extracted from an acidic solution by solvent extraction by a gallium extraction agent according to (1) or (2).

(4) In addition, the present invention is the gallium extraction method according to (3), wherein the amide derivative is a glycine amide derivative and the acidic solution is subjected to the solvent extraction with the pH of the acidic solution adjusted to a range of between 0.9 or more to 3.7 or less.

(5) In addition, the present invention is the gallium extraction method according to (3), wherein the amide derivative is a histidine amide derivative and the acidic solution is subjected to the solvent extraction with the pH of the acidic solution adjusted to a range of between 0.9 or more to 3.5 or less.

(6) In addition, the present invention is the gallium extraction method according to (3), wherein the amide derivative is a N-methylglycine derivative and the acidic solution is subjected to the solvent extraction with the pH of the acidic solution adjusted to a range of between 0.8 or more to 3.4 or less.

(7) In addition, the present invention is an gallium extraction method according to any of (3) to (6), wherein, an acidic solution with a pH of 0.8 or less is mixed with the extraction agent which has extracted the gallium from the acidic solution to carry out back extraction, and, thereafter, the extraction agent and the acidic solution are separated to obtain the acidic solution containing the gallium.

(8) In addition, the present invention is the gallium extraction method according to (7), wherein, an acidic solution is mixed with the extraction agent which has extracted the gallium from the acidic solution, and the extraction agent and the acidic solution are then separated to remove zinc from the extraction agent and the back extraction is then carried out.

(9) In addition, the present invention is the gallium extraction method according to (8), wherein the amide derivative is the glycine amide derivative, and an acidic solution with a pH of between 1.8 or more and 2.2 or less is mixed with the extraction agent which has extracted the gallium from the acidic solution, and the extraction agent and the acidic solution are then separated to remove zinc from the extraction agent and the back extraction is then carried out.

(10) In addition, the present invention is the gallium extraction method according to (8), wherein the amide derivative is the histidine amide derivative, and an acidic solution with a pH of between 2.6 or more and 3.0 or less is mixed with the extraction agent which has extracted the gallium from the acidic solution, and the extraction agent and the acidic solution are then separated to remove zinc from the extraction agent and the back extraction is then carried out.

(11) In addition, the present invention is the gallium extraction method according to (8), wherein the amide derivative is the N-methylglycine derivative, and an acidic solution with a pH of between 2.2 or more and 2.6 or less is mixed with the extraction agent which has extracted the gallium from the acidic solution, and the extraction agent and the acidic solution are then separated to remove zinc from the extraction agent and the back extraction is then carried out.

(12) In addition, the present invention is a gallium extraction method according to any of (3) to (11), wherein the acidic solution containing gallium and zinc is a solution obtained by mixing sulfuric acid with a member containing gallium and zinc and not containing cadmium and leaching gallium and zinc from the member.

Effects of the Invention

According to the present invention, unlike conventional extraction agents, gallium can be efficiently isolated from an acidic solution containing zinc at a high concentration even in the low pH region. In addition, the number of extraction steps can be decreased in actual operation and the equipment size can be compressed, and thus gallium can be recovered at a low cost.

PREFERRED MODE FOR CARRYING OUT THE INVENTION

Specific embodiments of the present invention will be now described in detail. It is noted, however, that the present invention is not limited to the following embodiments, and can be properly changed within the scope of the object of the present invention and carried out.

Extraction Agent

The extraction agent used for gallium extraction comprises an amide derivative represented by the following general formula (I).

In the formula, the substituents $R^1$ and $R^2$ each represent the same or different alkyl group. The alkyl group may be a straight chain or a branched chain. $R^3$ represents a hydrogen atom or an alkyl group. $R^4$ represents a hydrogen atom or any group other than an amino group which is bound to the α carbon as an amino acid. In the present invention, lipophilicity is enhanced by introducing an alkyl group into the amide skeleton and the present invention can be used as an extraction agent.

The above amide derivative is any one or more of a glycine amide derivative, a histidine amide derivative, a lysine amide derivative, an aspartic acid amide derivative and a N-methylglycine derivative (also referred to as a sarcosine amide derivative).

When the amide derivative is a glycine amide derivative, the above glycine amide derivative can be synthesized by the following method. First, a 2-halogenated acetyl halide is added to an alkyl amine having a structure represented by NHR$^1$R$^2$ (R$^1$ and R$^2$ are the same as the above substituents R$^1$ and R$^2$) and the hydrogen atom of the amine is substituted with a 2-halogenated acetyl by a nucleophilic substitution reaction to obtain a 2-halogenated (N,N-di)alkylacetamide.

Next, the above 2-halogenated (N,N-di)alkylacetamide is added to a glycine or N-alkyl glycine derivative, and one hydrogen atom of the glycine or N-alkyl glycine derivative is substituted with a (N,N-di)alkylacetamide group by a nucleophilic substitution reaction. With the two-step reaction, a glycine alkyl amide derivative can be synthesized.

It is noted that by replacing glycine with histidine, lysine, aspartic acid or N-methylglycine, a histidine amide derivative, a lysine amide derivative, an aspartic acid amide derivative or a N-methylglycine derivative can be synthesized.

Extraction of Gallium

To extract gallium ions using an extraction agent synthesized by the above method, the pH of an acidic aqueous solution containing gallium ions is adjusted and then the acidic solution is added to an organic solution having the above extraction agent as a component, and mixed. Therefore, an objective valuable metal ion can be selectively extracted in the organic phase. It is noted that by adjusting the above extraction agent to an appropriate concentration using a known diluent and the like as required, isolation ability can be improved and operation can be stabilized.

After the extraction of gallium ions, an acidic solution adjusted to a lower pH than that of the above acidic aqueous solution is added to the organic solvent as a back extraction starting solution and stirred to isolate an objective gallium ion by extraction to the organic solvent. Furthermore, by the back extraction of the objective gallium ion from the organic solvent, the objective gallium ion can be recovered in the aqueous solution. For example, an aqueous solution in which nitric acid, hydrochloric acid or sulfuric acid is diluted is suitably used as the back extraction solution. In addition, gallium ions can be also concentrated by properly changing the ratio of organic phase and aqueous phase.

The organic solvent can be any solvent in which an extraction agent and metal extraction species are dissolved, and examples thereof include chlorine solvents such as chloroform and dichloromethane, aromatic hydrocarbons such as benzene, toluene and xylene, aliphatic hydrocarbons such as hexane, and the like. These organic solvents may be used alone or two or more solvents may be used in combination. Alcohols such as 1-octanol may be mixed.

The concentration of the extraction agent can be properly set depending on the concentration of gallium. In addition, the stirring time and extraction temperature may be properly set depending on the conditions of the acidic aqueous solution of gallium ions and the organic solution of the extraction agent.

To efficiently recover gallium from an acidic aqueous solution containing gallium and zinc, by adding an alkali, an acid or the like to the acidic aqueous solution containing gallium and zinc, the acidic aqueous solution may be adjusted within the pH range in which gallium is extracted and the extraction of zinc is inhibited.

When extraction is carried out in the pH region in which the extraction rate of gallium is low, the amount of gallium extracted, i.e., the recovery rate declines. Contrarily, when extraction is carried out in the pH region in which the extraction rate is excessively high, zinc is also extracted and thus the purity of gallium recovered is decreased.

Multistep extraction is therefore industrially carried out in many cases. Indiscriminately increasing the number of extraction steps, however, is not preferred in terms of equipment investment and costs. Like the present invention, in particular, in the field which tries to isolate gallium from scrap and ores and the like, it is thought that extraction with 3 or 4 or less steps at the most is practical in terms of the liquid volume to be treated and the like. Because of this, the extraction rate of gallium in one step extraction is preferably 50% or more, more preferably 80% or more and even more preferably 95% or more. Contrarily, the extraction rate of zinc, which is an impurity, is preferably 20% or less and more preferably 10% or less.

The basic structure of the extraction agents used in the present invention is the same, but the small difference in optimum pH region is caused by a small difference in structure, and the agents can be properly used depending on the target liquids and conditions.

When the extraction agent is a glycine amide derivative, for example, the pH is preferably adjusted to between 0.7 or more and 3.7 or less and more preferably adjusted to between 1.4 or more and 2.2 or less.

In addition, when the extraction agent is a histidine amide derivative, the pH is preferably adjusted to between 0.9 or more and 3.5 or less and more preferably adjusted to between 2.3 or more and 2.9 or less.

In addition, when the extraction agent is a N-methylglycine derivative, the pH is preferably adjusted to between 0.8 or more and 3.4 or less and more preferably adjusted to between 1.8 or more and 2.7 or less.

By bringing an organic solution after extraction, with which gallium has been extracted, into contact with an acidic solution having a lower pH than that of the original acidic solution as a back extraction starting solution, incidentally, gallium in an extraction agent is distributed into the back extraction starting solution to recover gallium, and simultaneously the extraction agent can be regenerated. The pH of the back extraction starting solution is preferably low in the respect in which gallium can be recovered with high efficiency, but when the pH is too low, the recovery rate is not improved to more than a certain level and costs also increase. Further, when the pH is too low, there are problems in that, for example, the decomposition of an extraction agent is promoted. Therefore, the pH is preferably in the range of between 0.4 or more to 0.8 or less.

In addition, before the above back extraction of an extraction agent which has extracted gallium, the extraction agent is brought into contact with an acidic solution for washing (also referred to as scrubbing), thereby being able to isolate a part of the extracted zinc from the extraction agent. Consequently, the purity of gallium obtained by back extraction can be improved. When the range in which the extraction rate of gallium is 90 to 95% or more and the extraction rate of zinc is less than 20% is used as a standard, it is preferred that the acidic solution added in the washing step be between pH 1.8 or more and 2.2 or less in an extraction agent comprising a glycine amide derivative, between pH 2.6 or more and 3.0 or less in an extraction agent comprising a histidine amide derivative, and between pH 2.2 or more and 2.6 or less in an extraction agent comprising a sarcosine amide derivative.

EXAMPLES

The present invention will be now described in more detail by way of examples thereof. It is noted, however, that the present invention is not limited to these descriptions.

Synthetic Example 1 (Synthesis of Extraction Agent Comprising Glycine Amide Derivative)

As an example of amide derivatives forming an extraction agent, a glycine amide derivative represented by the following general formula (III) was synthesized, that is, N—[N,N-bis(2-ethylhexyl)aminocarbonylmethyl]glycine (or also referred to as N,N-di(2-ethylhexyl)acetamide-2-glycine, hereinafter referred to as "D2EHAG") into which two 2-ethylhexyl groups were introduced.

D2EHAG was synthesized as follows. First, as shown in the following reaction formula (II), 23.1 g (0.1 mol) of commercially available di(2-ethylhexyl)amine and 10.1 g (0.1 mol) of triethylamine were taken and chloroform was added thereto and dissolved. Next, 13.5 g (0.12 mol) of 2-chloroacetyl chloride was added dropwise thereto and the obtained mixture was washed once with 1 mol/l hydrochloric acid and then washed with ion exchanged water, and the chloroform phase was separated.

Next, anhydrous sodium sulfate was added thereto in an appropriate amount (approximately 10 to 20 g) for dehydration, followed by filtration to obtain 29.1 g of yellow liquid. The structure of this yellow liquid (reaction product) was identified using a nuclear magnetic resonance analyzer (NMR) and the above yellow liquid was confirmed to have the structure of 2-chloro-N,N-di(2-ethylhexyl)acetamide (hereinafter, referred to as "CDEHAA"). It is noted that the yield of CDEHAA was 90% with respect to di(2-ethylhexyl) amine, which is a raw material.

Next, as shown in the following reaction formula (III), 8.0 g (0.2 mol) of sodium hydroxide was dissolved by adding methanol, and 15.01 g (0.2 mol) of glycine were also added thereto. While stirring the obtained solution, 12.72 g (0.04 mol) of the above CDEHAA were slowly added dropwise thereto and stirred. After completion of stirring, the solvent in the reaction liquid was distilled off and the residue was dissolved by adding chloroform. This solution was acidified by adding 1 mol/l sulfuric acid and then washed with ion exchanged water, and the chloroform phase was separated.

Figure 1:
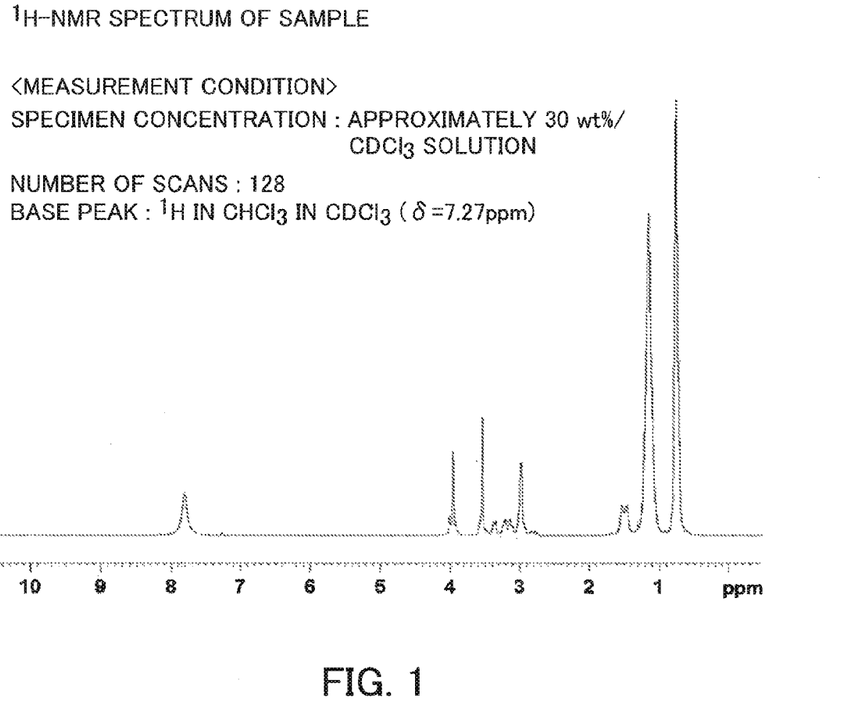
FIG. 1 is a diagram showing the $^1$H-NMR spectrum of a glycine amide derivative involved in Synthetic Example 1.
Figure 2:
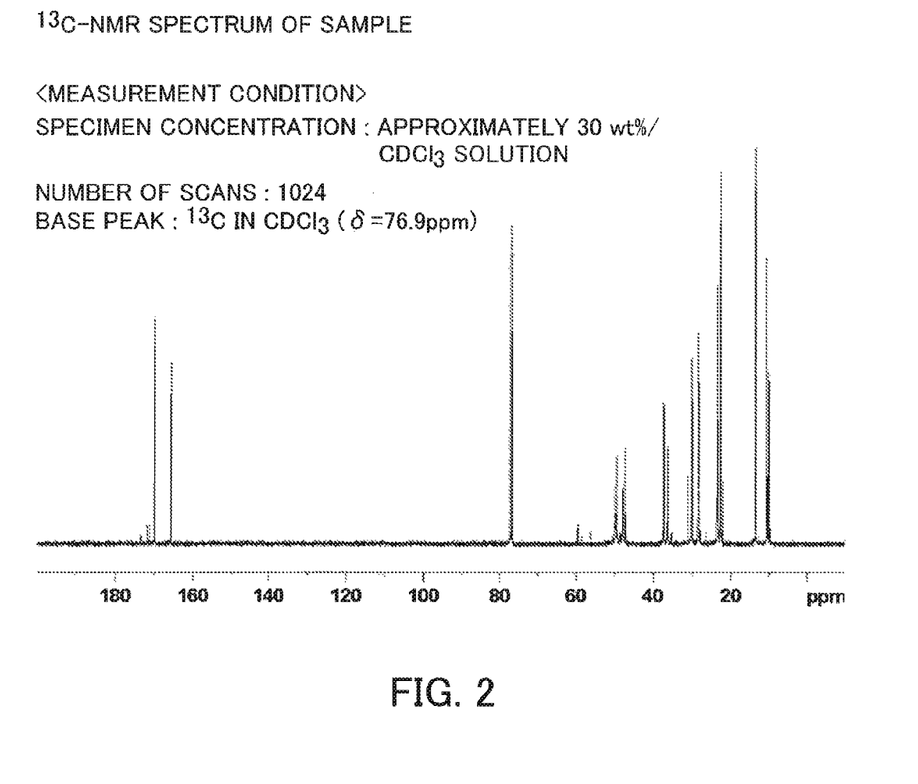
FIG. 2 is a diagram showing the $^{13}$C-NMR spectrum of a glycine amide derivative involved in Synthetic Example 1.

Anhydrous magnesium sulfate was added to this chloroform phase in an appropriate amount for dehydration, followed by filtration. The solvent was removed under reduced pressure again to obtain 12.5 g of yellow paste. The yield was 87% based on the amount of the above CDEHAA. The structure of the yellow paste was identified by NMR and elemental analysis and the yellow paste was confirmed to have the structure of D2EHAG as shown in FIG. 1 and FIG. 2. The extraction agent in Synthetic Example 1 was obtained by undergoing the above steps.

Synthetic Example 2 (Synthesis of Extraction Agent Comprising Histidine Amide Derivative)

As another example of amide derivatives forming an extraction agent, a histidine amide derivative represented by the following general formula (V) was synthesized, that is, N-[N,N-bis(2-ethylhexyl)aminocarbonylmethyl]histidine (or also referred to as N,N-di(2-ethylhexyl)acetamide-2-histidine, hereinafter referred to as "D2EHAH") into which two 2-ethylhexyl groups were introduced.

D2EHAH was synthesized as follows. As shown in the following reaction formula (V), 16 g (0.4 mol) of sodium hydroxide were dissolved by adding methanol, and 31.0 g (0.2 mol) of histidine were also added thereto. While stirring the obtained solution, 13.2 g (0.04 mol) of the above CDEHAA were slowly added dropwise thereto. After completion of dropwise addition, the solution was stirred with alkaline conditions maintained. After completion of stirring, the solvent in the reaction liquid was distilled off and the residue was dissolved by adding ethyl acetate. This solution was washed and the ethyl acetate phase was separated.

Anhydrous magnesium sulfate was added to this ethyl acetate phase in an appropriate amount for dehydration, followed by filtration. The solvent was removed under reduced pressure again to obtain 9.9 g of yellowish brown paste. The yield was 57% based on the amount of the above CDEHAA. The structure of the yellowish brown paste was identified by NMR and elemental analysis and the yellowish brown paste was confirmed to have the structure of D2EHAH. The extraction agent in Synthetic Example 3 was obtained by undergoing the above steps.

+ HCl

Synthetic Example 3 (Synthesis of Extraction Agent Comprising N-Methylglycine Derivative)

As another example of amide derivatives forming an extraction agent, a N-methylglycine derivative represented by the following general formula (IV) was synthesized, that is, N—[N,N-bis(2-ethylhexyl)aminocarbonylmethyl]sarcocine (or also referred to as N,N-di(2-ethylhexyl)acetamide-2-sarcocine, hereinafter referred to as "D2EHAS") into which two 2-ethylhexyl groups were introduced.

D2EHAS was synthesized as follows. As shown in the following reaction formula (IV), 5.3 g (0.132 mol) of sodium hydroxide were dissolved by adding methanol, and 11.8 g (0.132 mol) of sarcosine (N-methylglycine) were also added thereto. While stirring the obtained solution, 36.3 g (0.12 mol) of the above CDEHAA were slowly added dropwise thereto and stirred. After completion of stirring, the solvent in the reaction liquid was distilled off and the residue was dissolved by adding chloroform. This solution was acidified by adding 1 mol/l sulfuric acid and then washed with ion exchanged water, and the chloroform phase was separated.

Anhydrous magnesium sulfate was added to this chloroform phase in an appropriate amount for dehydration, followed by filtration. The solvent was removed under reduced pressure again to obtain 26.8 g of yellowish brown paste. The yield was 60% based on the amount of the above CDEHAA. The structure of the yellow paste was identified by NMR and elemental analysis and the yellow paste was confirmed to have the structure of D2EHAS. The extraction agent in Synthetic Example 2 was obtained by undergoing the above steps.

(IV)

Extraction of Gallium

Using the extraction agents in Synthetic Examples 1 to 3, gallium was extracted and isolated.

Example 1

An original liquid containing 8 mg/l gallium and 5 mg/l zinc was divided into 3 ml portions, and sulfuric acid was added to these to adjust the pH to from 0.8 to 3.7. The several types of sulfuric acidic solution and an n-dodecane solution with the same volume as above (3 ml) having the extraction agent involved in Synthetic Example 1 at a concentration of 0.01 mol/l were added to test tubes. The test tubes were put into a thermostatic chamber at 25° C. and shaken. At this time, the pH of the sulfuric acid solutions was adjusted using 0.1 mol/l nitric acid, ammonium nitrate and ammonia.

Figure 3:
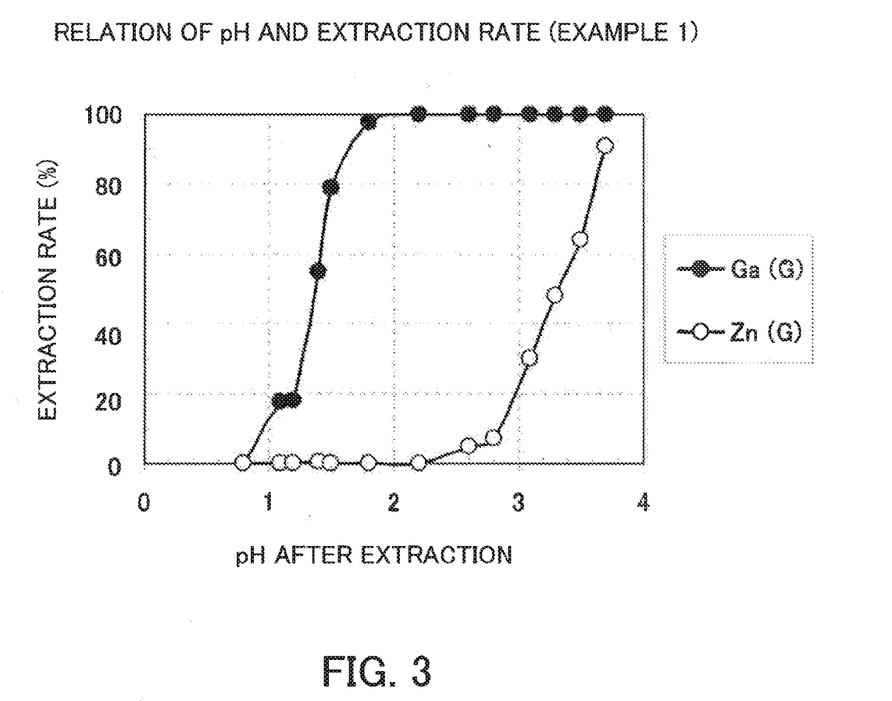
FIG. 3 shows the results when gallium was extracted from an acidic solution containing gallium and zinc using an extraction agent comprising a glycine amide derivative.

After shaking, the aqueous phase was separated and the concentration of gallium and the concentration of zinc were measured using an inductively coupled plasma-atomic emission spectrophotometer (ICP-AES). In addition, the organic phase was subjected to back extraction using 2 mol/l nitric acid. The concentration of gallium and the concentration of zinc in the back extraction phase were measured using ICP-AES. Using these measurement results, the extraction rates of gallium and zinc were defined by the amount of material in the organic phase/(the amount of material in the organic phase+the amount of material in the aqueous phase) and obtained. The results are shown in FIG. 3. In FIG. 3, the abscissa is the pH of sulfuric acidic solution and the ordinate is the extraction rate of gallium or zinc (unit: %). In the graph, a closed circle indicates the extraction rate of gallium and an open circle indicates the extraction rate of zinc.

Example 2

Figure 4:
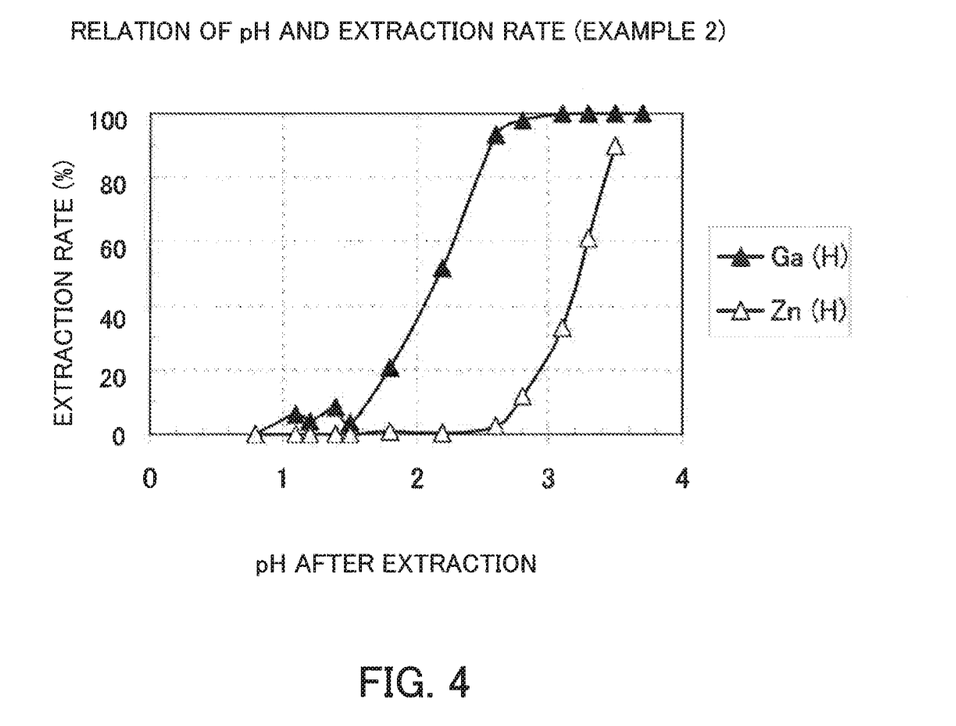
FIG. 4 shows the results when gallium was extracted from an acidic solution containing gallium and zinc using an extraction agent comprising a histidine amide derivative.

Gallium was extracted from a sulfuric acidic solution containing gallium and zinc in the same method as in Example 1 except that the extraction agent involved in Synthetic Example 2 was used as the extraction agent in place of the extraction agent involved in Synthetic Example 1. The results are shown in FIG. 4. In FIG. 4, the abscissa is the pH of sulfuric acidic solution and the ordinate is the extraction rate of gallium or zinc (unit: %). In the graph, a closed triangle indicates the extraction rate of gallium and an open triangle indicates the extraction rate of zinc.

Example 3

Figure 5:
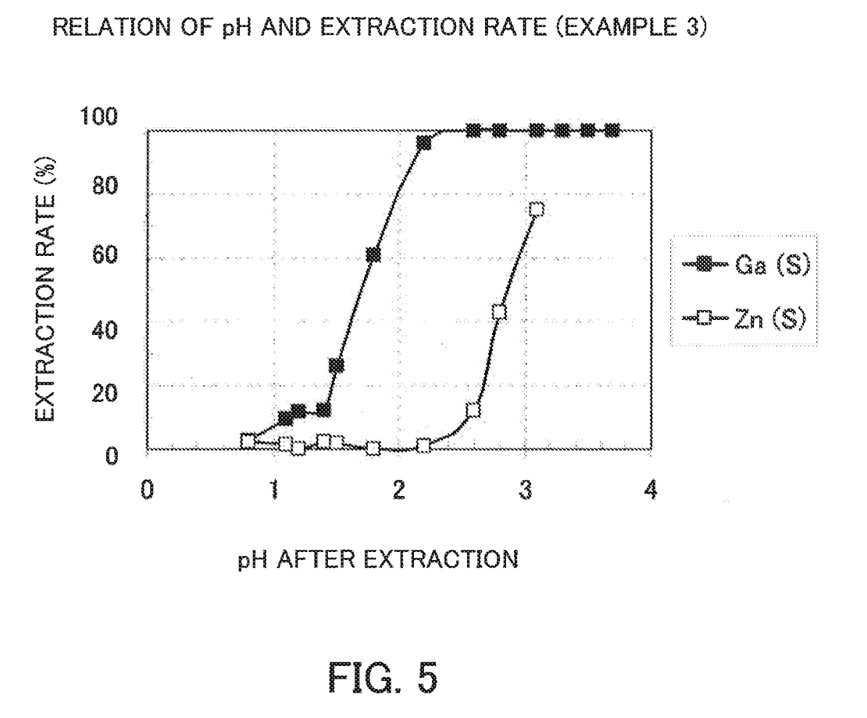
FIG. 5 shows the results when gallium was extracted from an acidic solution containing gallium and zinc using an extraction agent comprising a N-methylglycine derivative.

Gallium was extracted from a sulfuric acidic solution containing gallium and zinc in the same method as in Example 1 except that the extraction agent involved in Synthetic Example 3 was used as the extraction agent in place of the extraction agent involved in Synthetic Example 1. The results are shown in FIG. 5. In FIG. 5, the abscissa is the pH of sulfuric acidic solution and the ordinate is the extraction rate of gallium or zinc (unit: %). In the graph, a closed square indicates the extraction rate of gallium and an open square indicates the extraction rate of zinc.

Figure 6:
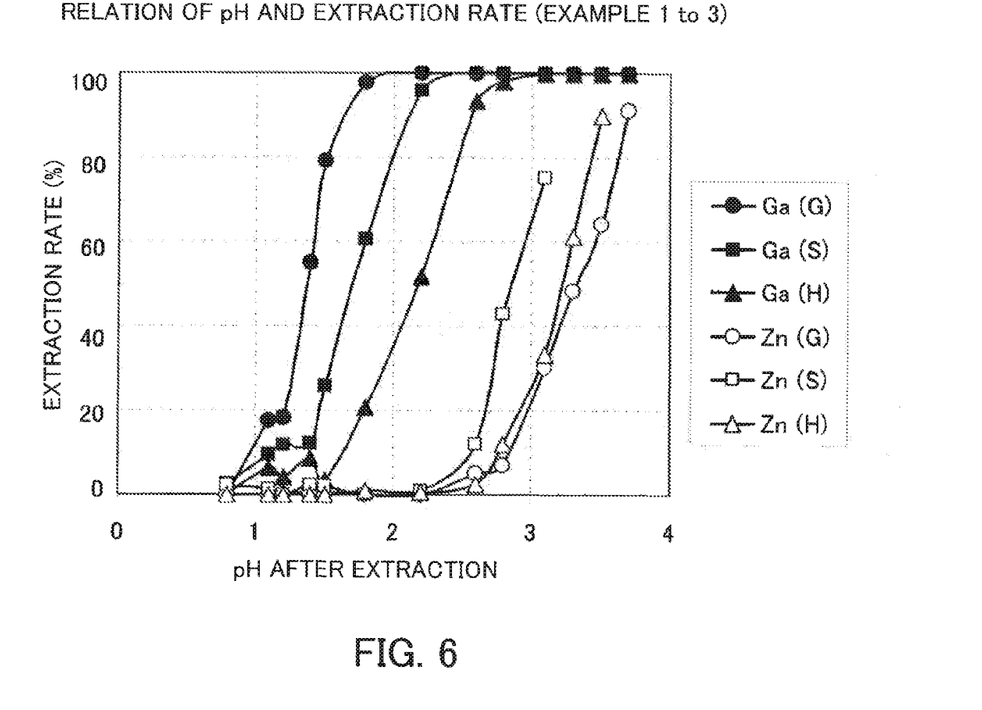
FIG. 6 is a diagram summarizing the results shown in FIG. 3 to FIG. 5 in a graph.

It was verified that gallium could be efficiently extracted from a sulfuric acidic solution containing gallium and zinc using the extraction agents in Synthetic Examples 1 to 3 (FIG. 3 to FIG. 5). In addition, the differences depending on the types of extraction agent are considered, and isolation can be carried out even in a wide pH range by using an extraction agent comprising a glycine amide derivative as shown in FIG. 6, and it is thought that it is easiest to use this agent in industry. The range of the pH region suitable for isolation with extraction agents comprising a sarcosine alkyd amide and a histidine alkyl amide is not as wide as that of an extraction agent comprising a glycine amide derivative. An extraction agent comprising a sarcosine alkyd amide is suitable for isolation at a lower pH than that in an extraction agent comprising a histidine alkyl amide.

Furthermore, extraction agents using amino acids having a lysine amide derivative and an aspartic acid amide derivative as a main component can be considered. The extraction behaviors of these agents are the same as when using the extraction agents involved in Synthetic Examples 1 to 3 in view of complex stability constants thereof. Therefore, it is inferred that gallium can be efficiently isolated.

The invention claimed is:

1. A gallium extraction agent comprising:
a solution comprising an organic solvent and an amide derivative,
wherein
the amide derivative is represented by the formula:

wherein, $R_1$ and $R_2$ each represent the same or different straight chain or branched chain alkyl group, and
$R_3$ represents a hydrogen atom or an alkyl group.

2. A gallium extraction method, comprising:
extracting gallium from an acidic solution by subjecting the acidic solution to solvent extraction with a gallium extraction agent comprising an amide derivative represented by formula:

wherein, $R_1$ and $R_2$ each represent the same or different straight chain or branched chain alkyl group, and
$R_3$ represents a hydrogen atom or an alkyl group.

3. The gallium extraction method according to claim 2, wherein $R_3$ is H, and
the acidic solution is subjected to the solvent extraction with the pH of the acidic solution adjusted to a range of between 0.9 to 3.7.

4. The gallium extraction method according to claim 2, wherein $R_3$ is H, and
the acidic solution is subjected to the solvent extraction with the pH of the acidic solution adjusted to a range of between 0.9 to 3.5.

5. The gallium extraction method according to claim 2, wherein
the acidic solution is subjected to the solvent extraction with the pH of the acidic solution adjusted to a range of between 0.8 to 3.4.

6. The gallium extraction method according to claim 2, wherein an acidic solution with a pH of 0.8 or less is mixed with the extraction agent which has extracted the gallium from the acidic solution to carry out back extraction, and, thereafter, the extraction agent and the acidic solution are separated to obtain the acidic solution containing the gallium.

7. The gallium extraction method according to claim 6, wherein the acidic solution further comprises zinc and the acidic solution is mixed with the extraction agent which has extracted the gallium from the acidic solution, and the extraction agent and the acidic solution are then separated to remove zinc from the extraction agent and the back extraction is then carried out.

8. The gallium extraction method according to claim 2, wherein the acidic solution further comprises zinc and wherein $R_3$ is H, and
an acidic solution with a pH of between 1.8 or more and 2.2 is mixed with the extraction agent which has extracted the gallium from the acidic solution, and the extraction agent and the acidic solution are then separated to remove zinc from the extraction agent and an acidic solution with a pH of 0.8 or less is then mixed with the extraction agent to carry out back extraction, and, thereafter, the extraction agent and the acidic solution are separated to obtain the acidic solution containing the gallium.

9. The gallium extraction method according to claim 2, wherein the acidic solution further comprises zinc and wherein $R_3$ is H, and
an acidic solution with a pH of between 2.6 and 3.0 is mixed with the extraction agent which has extracted the gallium from the acidic solution, and the extraction agent and the acidic solution are then separated to remove zinc from the extraction agent, and an acidic solution with a pH of 0.8 or less is then mixed with the extraction agent to carry out back extraction, and, thereafter, the extraction agent and the acidic solution are separated to obtain the acidic solution containing the gallium.

10. The gallium extraction method according to claim 2, wherein,
an acidic solution with a pH of between 2.2 and 2.6 is mixed with the extraction agent which has extracted the gallium from the acidic solution, and the extraction agent and the acidic solution are then separated to remove zinc from the extraction agent, and an acidic solution with pH of 0.8 or less is then mixed with the extraction agent to carry out back extraction, and, thereafter, the extraction agent and the acidic solution are separated to obtain the acidic solution containing the gallium.

11. The gallium extraction method according to claim 2, wherein the acidic solution further comprises zinc and wherein the acidic solution containing gallium and zinc is a solution obtained by mixing sulfuric acid with a material containing gallium and zinc and not containing cadmium and leaching gallium and zinc from the material.

12. The gallium extraction method according to claim 3, wherein an acidic solution with a pH of 0.8 or less is mixed with the extraction agent which has extracted the gallium from the acidic solution to carry out back extraction, and, thereafter, the extraction agent and the acidic solution are separated to obtain the acidic solution containing the gallium.

13. The gallium extraction method according to claim 4, wherein an acidic solution with a pH of 0.8 or less is mixed with the extraction agent which has extracted the gallium from the acidic solution to carry out back extraction, and, thereafter, the extraction agent and the acidic solution are separated to obtain the acidic solution containing the gallium.

14. The gallium extraction method according to claim 5, wherein an acidic solution with a pH of 0.8 or less is mixed with the extraction agent which has extracted the gallium from the acidic solution to carry out back extraction, and, thereafter, the extraction agent and the acidic solution are separated to obtain the acidic solution containing the gallium.

15. The gallium extraction method according to claim 3, wherein $R_3$ is H, and
an acidic solution with a pH of between 1.8 and 2.2 is mixed with the extraction agent which has extracted the gallium from the acidic solution, and the extraction agent and the acidic solution are then separated to remove zinc from the extraction agent and an acidic solution with a pH of 0.8 or less is then mixed with the extraction agent to carry out back extraction, and, thereafter, the extraction agent and the acidic solution are separated to obtain the acidic solution containing the gallium.

16. The gallium extraction method according to claim 4, wherein the acidic solution further comprises zinc and wherein $R_3$ is H, and
an acidic solution with a pH of between 2.6 and 3.0 is mixed with the extraction agent which has extracted the gallium from the acidic solution, and the extraction agent and the acidic solution are then separated to remove zinc from the extraction agent, and an acidic solution with a pH of 0.8 or less is then mixed with the extraction agent to carry out back extraction and, thereafter, the extraction agent and the acidic solution are separated to obtain the acidic solution containing the gallium.

17. The gallium extraction method according to claim 5, wherein the acidic solution further comprises zinc and wherein
an acidic solution with a pH of between 2.2 and 2.6 is mixed with the extraction agent which has extracted the gallium from the acidic solution, and the extraction agent and the acidic solution are then separated to remove zinc from the extraction agent, and an acidic solution with a pH of 0.8 or less is then mixed with the extraction agent to carry out back extraction, and, thereafter, the extraction agent and the acidic solution are separated to obtain the acidic solution containing the gallium.

18. The gallium extraction method according to claim 8, wherein the acidic solution containing gallium and zinc is a solution obtained by mixing sulfuric acid with a material containing gallium and zinc and not containing cadmium and leaching gallium and zinc from the material.

19. The gallium extraction method according to claim 9, wherein the acidic solution containing gallium and zinc is a solution obtained by mixing sulfuric acid with a material containing gallium and zinc and not containing cadmium and leaching gallium and zinc from the material.

* * * * *